United States Patent [19]

Katz

[11] 4,343,803
[45] Aug. 10, 1982

[54] 2-TRICHLOROMETHYL-4-PYRIMIDINYL CARBAMATES AND THEIR USE AS FUNGICIDES

[75] Inventor: Lawrence E. Katz, Orange, Conn.

[73] Assignee: Olin Corporation, New Haven, Conn.

[21] Appl. No.: 259,792

[22] Filed: May 4, 1981

[51] Int. Cl.³ .................... A01N 43/54; C07D 239/34
[52] U.S. Cl. ...................................... 424/251; 544/319
[58] Field of Search ......................... 544/319; 424/251

[56] References Cited

U.S. PATENT DOCUMENTS 4,200,637   4/1980   Maurer et al. ...................... 544/319
4,234,587  11/1980   Maurer et al. ...................... 544/319

*Primary Examiner*—Paul M. Coughlan, Jr.
*Attorney, Agent, or Firm*—William D. Sabo

[57] ABSTRACT

Disclosed are selected 2-trichloromethyl-4-pyrimidinyl carbamates having the formula:

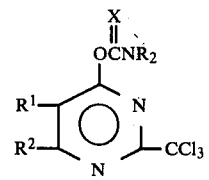

wherein X is an atom selected from the group consisting of oxygen and sulfur; R is a lower alkyl group having 1 to 4 carbon atoms or a phenyl group or $R_2$ is —($CH_2$)$_n$—, where n is 4 or 5; $R^1$ is hydrogen, a lower alkyl group having 1 to 4 carbon atoms, halo or nitro; and $R^2$ is a lower alkyl group having 1 to 4 carbon atoms or a halo alkyl group having 1 to 4 carbon atoms. These compounds are disclosed to be agricultural fungicides.

26 Claims, No Drawings

2-TRICHLOROMETHYL-4-PYRIMIDINYL CARBAMATES AND THEIR USE AS FUNGICIDES

BACKGROUND OF THE INVENTION

1. Field of the Invention

This invention relates to selected 2-trichloromethyl-4-pyrimidinyl carbamates and their use as fungicides.

2. Description of the Prior Art

British Pat. No. 1,181,657 discloses the use of 5,6-dimethyl-2-dimethylamino-4-pyrimidinyl dimethylcarbamate as an insecticide.

BRIEF SUMMARY OF THE INVENTION

Accordingly, the present invention is directed to, as compositions of matter, selected 2-trichloromethyl-4-pyrimidinyl carbamates having the formula:

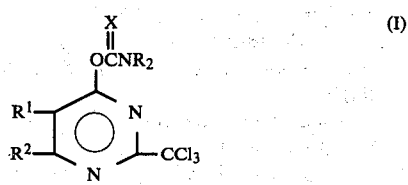

wherein X is an atom selected from the group consisting of oxygen and sulfur; R is a lower alkyl group having 1 to 4 carbon atoms or a phenyl group or $R_2$ is $-(CH_2)_n-$, where n is 4 or 5; $R^1$ is hydrogen, a lower alkyl group having 1 to 4 carbon atoms, halo or nitro; and $R^2$ is a lower alkyl group having 1 to 4 carbon atoms or a haloalkyl group having 1 to 4 carbon atoms. It is to be understood that the term "halo" as used in the specification and claims herein is intended to include fluoro, chloro, bromo and iodo. The present invention is also directed to the use of these compounds as fungicides.

DETAILED DESCRIPTION

The pyrimidinyl carbamate compounds of the present invention may be prepared by reacting trichloroacetamidine with the corresponding acetoacetate to form the corresponding 4-hydroxy-2-trichloromethylpyrimidine, which is then reacted with a selected carbamoyl chloride. These general reactions are illustrated below in equations (A) and (B). In equation (A), trichloroacetamidine is reacted with methylacetoacetate to form 4-hydroxy-6-methyl-2-trichloromethylpyrimidine. In equation (B), the 4-hydroxy-6-methyl-2-trichloromethylpyrimidine is reacted with dimethylcarbamoyl chloride to form 6-methyl-2-trichloromethyl-4-pyrimidinyl dimethylcarbamate.

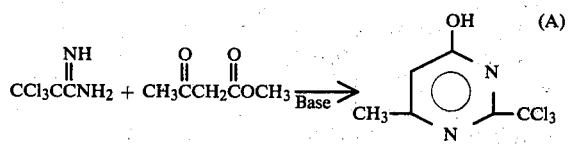

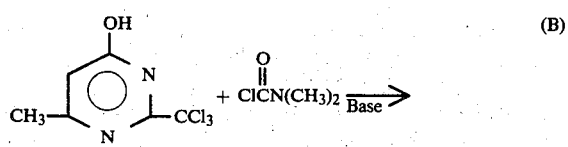

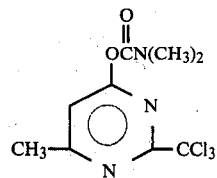

The trichloroacetamidine reactant is made by reacting trichloroacetonitrile with ammonia. Trichloroacetonitrile is a commercially available material. See German Pat. No. 671,785.

The acetoacetate reactants may be made by reacting the corresponding acetate with a suitable condensing agent such as sodium ethoxide. See Hickenbottom, W. J., Reactions of Organic Compounds (3rd Edition), pages 359 and 360 (1957). For example, ethyl acetate may be treated with sodium ethoxide, and the resulting mixture acidified to form ethyl acetoacetate. Various acetoacetates such as methyl acetoacetate and ethyl acetoacetate are commercially available.

Illustrative acetoacetate reactants for the compounds of the present invention include the following:
  ethyl acetoacetate
  methyl acetoacetate
  ethyl 2-chloroacetoacetate
  ethyl 4-chloroacetoacetate
  ethyl butyrylacetate.

The carbamoyl chloride reactants may be made by reacting the corresponding secondary amine with phosgene or thiophosgene. See Franchimant, A. P. N. and Ronffaer, H. A., Rec. Trav. Chim., 13, 331 (1894). For example, dimethylamine may be reacted with phosgene to produce dimethylcarbamoyl chloride.

Illustrative carbamoyl chloride reactants for the compounds of the present invention include the following:
  dimethylcarbamoyl chloride
  diethylcarbamoyl chloride
  diphenylcarbamoyl chloride
  1-pyrrolidinecarbonyl chloride
  dimethylthiocarbamoyl chloride
  diethylthiocarbamoyl chloride
  diphenylthiocarbamoyl chloride.

Any suitable conventional reaction conditions may be employed in the synthesis of the 4-hydroxy-2-trichloromethylpyrimidine compounds. See Henze et al., J. Org. Chem., 17, 1320 (1952); Falch et al., J. Med. Chem., 11, 608 (1968); and U.S. Pat. No. 3,118,889 as examples of such a synthesis.

A wide variety of conventional reaction conditions may be employed in the synthesis of the present compounds according to equation (B) and the present invention is not intended to be limited to any particular reaction conditions. For example, carbamoylation of the hydroxyl group of the 4-hydroxy-2-trichloromethylpyrimidine compound can be carried out by reacting the 4-hydroxy-2-trichloromethylpyrimidine compound with a selected carbamoyl chloride in the presence of a base such as triethylamine, pyridine, sodium carbonate or potassium carbonate. Advantageously and preferably, the reactions are performed with an equimolar amount of carbamoyl chloride to the 4-hydroxy-2-trichloromethylpyrimidine compound, although a slight excess of the former may be used (e.g. from about 0.01 to about 1.0 mole excess). It is also preferred to use an equimolar amount of the base to the carbamoyl chloride, although lesser or greater amounts can be employed. A solvent is not necessary, but any suitable inert solvent such as acetonitrile or diethyl ether may be employed.

Furthermore, the reaction temperature and time will both depend upon many factors including the exact reactants being employed. In most situations, reaction temperatures from about 30° C. to about 100° C. and reaction times from about 2 hours to about 72 hours are preferred.

The desired product may be recovered from the reaction mixture by any conventional means, for example, extraction, recrystallization, or the like. Finally, it should be noted that while the reactions illustrated by equations (A) and (B) are preferred, other synthesis methods for preparing compounds of the present invention may also be employed.

Representative compounds of the present invention include the following:

6-methyl-2-trichloromethyl-4-pyrimidinyl dimethylcarbamate 6-methyl-2-trichloromethyl-4-pyrimidinyl diethylcarbamate 6-methyl-2-trichloromethyl-4-pyrimidinyl diphenylcarbamate 6-methyl-4-(1-pyrrolidinylcarboxy)-2-trichloromethyl-pyrimidine 6-methyl-2-trichloromethyl-4-pyrimidinyl dimethylthiocarbamate 6-methyl-2-trichloromethyl-4-pyrimidinyl diethylthiocarbamate 6-methyl-2-trichloromethyl-4-pyrimidinyl diphenylthiocarbamate 6-chloromethyl-2-trichloromethyl-4-pyrimidinyl dimethylcarbamate 5-chloro-6-methyl-2-trichloromethyl-4-pyrimidinyl dimethylcarbamate 5-ethyl-6-methyl-2-trichloromethyl-4-pyrimidinyl dimethylcarbamate 6-methyl-5-nitro-2-trichloromethyl-4-pyrimidinyl dimethylcarbamate 6-chloromethyl-5-methyl-2-trichloromethyl-4-pyrimidinyl dimethylcarbamate 5-chloro-6-dichloromethyl-2-trichloromethyl-4-pyrimidinyl diphenylcarbamate.

Also, in accordance with the present invention, it has been found that the compounds of Formula (I) above, may be utilized as effective foliar or soil fungicides. In practicing the process of the present invention, fungi are contacted with a fungicidally effective amount of one or more of these compounds. It is to be understood that the term "fungicidally effective amount" as used in the specification and claims herein is intended to include any amount that will kill or control said foliar or soil fungi when either employed by itself (i.e., in full concentration) or in sufficient concentrations within a carrier or other substance. Of course, this amount may be constantly changing because of the possible variations in many parameters. Some of these may include: the number and type of fungi to be controlled or killed; the type of media to which the present compound can be applied (e.g. plants or soil); degree of effectiveness required; and type of carrier, if any. Generally speaking, applications of an aqueous spray containing at least about 20, more preferably in the range of about 30 to 300, parts per million of the chemical of the present invention may give satisfactory fungi control for most crops.

This step of contacting may be accomplished by applying this compound to the fungi themselves, their habitat, dietary media such as vegetation, crops and the like, including many which these pests may attack.

The above-mentioned compounds of the present invention may be formulated and applied by any conventional methods that include using the compound alone or with a carrier or other substances which may enhance the effectiveness of the chemical or facilitate handling. Moreover, the activity of the present compound may be broadened by the addition thereto of other known pesticides such as other fungicides, herbicides, insecticides and the like.

Specific methods of formulating and applying these active compounds include applying them in the form of dusts, dust or emulsion concentrates, wettable powders and concentrates, granulates, dispersions, sprays, solutions and the like.

The dusts are usually prepared by simply grinding together from about 1% to about 15% by weight of the active compound with a finely divided inert diluent such as walnut flour, diatomaceous earth, fullers earth, attaclay, talc or kaolin.

Dust concentrates are made in similar fashion except that about 16% to about 75% by weight of active compound is ground usually together with the diluent. In practice, dust concentrates are then generally admixed at the site of use with more inert diluent before it is applied to the plant foliage, soil or animals which are to be protected from fungi attack.

Wettable powders are generally prepared in the same manner as dust concentrates, but usually about 1% to about 10% by weight of a dispersing agent, for example, an alkali metal lignosulfonate and about 1% to about 10% of a surfactant, such as a non-ionic surfactant, are incorporated in the formulation. For application to agronomic crops, shrubs, ornamentals and the like, the wettable powder is usually dispersed in water and applied as a spray.

Emulsifiable liquids may be prepared by dissolving the active compound in an organic solvent, such as xylene or acetone, and admixing the thus formed solution with a surfactant or an emulsifier. The emulsified liquid is then generally dispersed in water for spray or dip application.

It is possible to formulate granulates whereby the active compound is dissolved in an organic solvent and the resulting solution is then applied to a granulated mineral or the like (e.g., bentonite, $SiO_2$, or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, the above-mentioned active compound is normally dissolved in a suitable organic solvent, solvent mixtures or water. As organic solvents, it is possible to use any suitable aliphatic and aromatic hydrocarbon or their derivatives. It is preferred that the solvent be odorless and, moreover, be inert to the active compound.

It should be clearly understood that the fungicide formulations, the ingredients which may make up such formulations other than the active compound, the dosages of these ingredients, and means of applying these formulations may include all known and conventional substances, amounts and means, respectively, that are suitable for obtaining the desired fungicidal result. And, therefore, such process parameters are not critical to the present invention.

Fungicides of the present invention may be effective for the control of broad classes of foliar and soil fungi. Specific illustrations of foliar fungi wherein fungicidal activity has been shown include cucumber anthracnose and potato late blight. A specific illustration of soil fungus wherein fungicidal activity has been shown is pythium.

The following examples further illustrate the present invention. All parts and percentages employed therein are by weight unless otherwise indicated. Yields given are percent molar yields.

EXAMPLE 1

Preparation of 4-Hydroxy-6-Methyl-2-Trichloromethylpyrimidine

A mixture of 44.4 g (0.28 mole) trichloroacetamidine, 32.0 g (0.28 mole) methylacetoacetate, 37.5 g (0.28 mole) potassium carbonate, and 450 ml water was stirred for 3 days. A trace of solid was removed by filtration and the filtrate was made acidic with hydrochloric acid. The product precipitated out to give 28.9 g (46% yield; mp 173°–174° C.). The structure was confirmed via mp*, infrared and elemental analysis.
*J. Med. Chem., 11, 608 (1968).

Analysis for $C_6H_5N_2Cl_3O$:

|  | C | H | N | Cl |
|---|---|---|---|---|
| Calculated: | 31.68 | 2.22 | 12.32 | 46.76 |
| Found: | 31.37 | 2.26 | 12.31 | 46.86 |

EXAMPLE 2

Preparation of 6-Methyl-2-Trichloromethyl-4-Pyrimidinyl Dimethylcarbamate

A mixture of 5.7 g (0.025 mole) 4-hydroxy-6-methyl-2-trichloromethylpyrimidine, 5.1 g (0.05 mole) triethylamine, and 100 ml acetonitrile was stirred and 5.4 g (0.05 mole) dimethylcarbamoyl chloride was added to the mixture. The reaction mixture was stirred 2 hours under reflux, and allowed to cool. A solid was filtered out after cooling and washed with water to give 3.6 g (48% yield; mp 83.5°–84.5° C.). The structure was confirmed via infrared and elemental analysis.

Analysis for $C_9H_{10}N_3Cl_3O_2$:

|  | C | H | N | Cl |
|---|---|---|---|---|
| Calculated: | 36.20 | 3.38 | 14.07 | 35.63 |
| Found: | 36.32 | 3.29 | 14.18 | 35.93 |

EXAMPLE 3

Preparation of 6-Methyl-2-Trichloromethyl-4-Pyrimidinyl Diphenylcarbamate

To a mixture of 5.7 g (0.025 mole) 4-hydroxy-6-methyl-2-trichloromethylpyrimidine, 2.6 g (0.025 mole) triethylamine, and 100 ml acetonitrile was added 5.8 g (0.025 mole) diphenylcarbamoyl chloride. The reaction mixture was refluxed 4 hours. A precipitate was filtered out and ether was added to the filtrate yielding more precipitate. Rotary evaporation gave 9.3 g residue which was recrystallized from ligroin to give 6.15 g (58% yield) of product. An analytical sample was recrystallized a second time from ligroin and had mp 132°–134° C. The structure was confirmed via infrared and elemental analysis.

Analysis for $C_{19}H_{14}N_3Cl_3O_2$:

|  | C | H | N | Cl |
|---|---|---|---|---|
| Calculated: | 53.99 | 3.34 | 9.94 | 25.17 |
| Found: | 53.67 | 3.50 | 10.28 | 24.95 |

EXAMPLE 4

Preparation of 6-Methyl-2-Trichloromethyl-4-Pyrimidinyl Dimethylthiocarbamate

A mixture of 5.7 g (0.025 mole) 4-hydroxy-6-methyl-2-trichloromethylpyrimidine, 2.6 g (0.025 mole) triethylamine, 3.2 g (0.025 mole) dimethylthiocarbamoyl chloride, and 100 ml ether was refluxed 16 hours. A trace of dark solid was filtered out and the solution was evaporated on a steam bath to give a solid residue. This residue was extracted with hot ligroin to yield 4.3 g (55% yield) of product (mp 81°–83° C.) on cooling. The structure was confirmed via infrared and elemental analysis.

Analysis for $C_9H_{10}N_3Cl_3SO$:

|  | C | H | N | Cl | S |
|---|---|---|---|---|---|
| Calculated: | 34.36 | 3.20 | 13.36 | 33.81 | 10.19 |
| Found: | 34.17 | 3.43 | 13.06 | 34.02 | 10.13 |

EXAMPLE 5

Preparation of 5-Chloro-4-Hydroxy-6-Methyl-2-Trichloromethylpyrimidine

A mixture of 30.0 g (0.18 mole) trichloroacetamidine, 25.2 g (0.18 mole) potassium carbonate, 30.3 g (0.18 mole) ethyl 2-chloroacetoacetate, and 300 ml water was stirred 18 hours. The aqueous solution was decanted from heavier tars and acidified with hydrochloric acid. The precipitate that was formed was filtered, washed, and dried to give 14.7 g (31% yield; mp 130°–145° C.) of crude product. An analytical sample recrystallized from cyclohexane had mp 156°–157° C. The structure was confirmed via infrared and elemental analysis.

Analysis for $C_6H_4N_2Cl_4O$:

|  | C | H | N | Cl |
|---|---|---|---|---|
| Calculated: | 27.51 | 1.54 | 10.74 | 54.15 |
| Found: | 28.20 | 1.88 | 11.00 | 52.54 |

EXAMPLE 6

Preparation of 5-Chloro-6-Methyl-2-Trichloromethyl-4-Pyrimidinyl Dimethylcarbamate A mixture of 3.9 g (0.015 mole) 5-chloro-4-hydroxy-6-methyl-2-trichloromethylpyrimidine, 1.6 g (0.015 mole) triethylamine, 1.7 g (0.015 mole) dimethylcarbamoyl chloride, and 80 ml acetonitrile was refluxed 3 days. Rotary evaporation to concentrate the solution yielded a precipitate that was removed by filtration. Rotary evaporation of the filtrate gave a residue which was triturated with petroleum ether to give 1.0 g (20% yield; mp 87°–88° C.) of product. The structure was confirmed via infrared and elemental analysis.

Analysis for $C_9H_9N_3Cl_4O_2$:

|  | C | H | N | Cl |
|---|---|---|---|---|
| Calculated: | 32.46 | 2.72 | 12.62 | 42.59 |
| Found: | 32.37 | 2.90 | 12.46 | 42.78 |

EXAMPLE 7

Preparation of 6-Chloromethyl-4-Hydroxy-2-Trichloromethylpyrimidine

A mixture of 30.0 g (0.18 mole) trichloroacetamidine, 25.2 g (0.18 mole) potassium carbonate, 30.3 g (0.18 mole) ethyl-4-chloroacetoacetate and 400 ml water was stirred 18 hours. The aqueous solution was filtered and acidified with hydrochloric acid to give a precipitate. The precipitate was washed and dried to give 17.0 g (36% yield) of crude product. An analytical sample recrystallized from ligroin had mp 138°–144° C. The structure was confirmed via infrared and elemental analysis.

Analysis for $C_6H_4N_2Cl_4O$:

|  | C | H | N | Cl |
|---|---|---|---|---|
| Calculated: | 27.51 | 1.54 | 10.70 | 54.15 |
| Found: | 27.33 | 1.72 | 10.90 | 54.35 |

EXAMPLE 8

Preparation of 6-Chloromethyl-2-Trichloromethyl-4-Pyrimidinyl Dimethylcarbamate

A solution of 1.3 g (0.005 mole) 6-chloromethyl-4-hydroxy-2-trichloromethylpyrimidine, 0.55 g (0.005 mole) triethylamine, 0.55 g (0.005 mole) dimethylcarbamoyl chloride and 25 ml ether was refluxed 20 hours. The solvent was rotary evaporated and the residue extracted with refluxing ligroin. The extract was cooled to yield 1.0 g (60% yield) of pure product as a thick oil. The structure was confirmed via infrared and elemental analysis.

Analysis for $C_9H_9N_3Cl_4O_2$:

|  | C | H | N | Cl |
|---|---|---|---|---|
| Calculated: | 32.46 | 2.72 | 12.62 | 42.59 |
| Found: | 32.80 | 2.64 | 13.38 | 42.24 |

EXAMPLE 9

Preparation of 6-Methyl-2-Trichloromethyl-4-Pyrimidinyl Diethylcarbamate

A mixture of 5.8 g (0.027 mole) 4-hydroxy-6-methyl-2-trichloromethylpyrimidine, 3.3 g (0.024 mole) potassium carbonate, 3.3 g (0.024 mole) dimethylcarbamoyl chloride, and 100 ml acetone was refluxed 5 hours. A precipitate was filtered out and the filtrate rotary evaporated to give 10.2 g residue. This was taken up in chloroform, the solution washed with 1% sodium hydroxide, water, and dried over anhydrous magnesium sulfate. Rotary evaporation yielded 5.2 g residue which was recrystallized from petroleum ether to give 2.1 g (24% yield) of product. An analytical sample recrystallized a second time from petroleum ether had mp 77°–77.5° C. The structure was confirmed via infrared and elemental analysis.

Analysis for $C_{11}H_{14}N_3Cl_3O_2$:

|  | C | H | N | Cl |
|---|---|---|---|---|
| Calculated: | 40.45 | 4.32 | 12.87 | 32.57 |
| Found: | 40.35 | 4.25 | 12.82 | 32.80 |

EXAMPLE 10

Preparation of 6-Methyl-4-(1-Pyrrolidinylcarboxy)-2-Trichloromethylpyrimidine

A mixture of 5.8 g (0.027 mole) 4-hydroxy-6-methyl-2-trichloromethylpyrimidine, 3.3 g (0.024 mole) potassium carbonate, 3.2 g (0.024 mole) pyrrolidinecarbonyl chloride, and 100 ml acetone was refluxed 5.3 hours. A precipitate was filtered out and the filtrate rotary evaporated to give 9.8 g residue. This was taken up in chloroform, the solution washed with 1% sodium hydroxide, water, and dried over anhydrous magnesium sulfate. Rotary evaporation yielded 4.4 g residue which was recrystallized from petroleum ether to give 2.2 g (28% yield; mp 93°–95° C.) of product. The structure was confirmed via infrared and elemental analysis.

Analysis for $C_{11}H_{12}N_3Cl_3O_2$:

|  | C | H | N | Cl |
|---|---|---|---|---|
| Calculated: | 40.70 | 3.73 | 12.95 | 32.77 |
| Found: | 40.40 | 3.59 | 13.09 | 33.04 |

Foliar Fungicide Screen

The active material formed in Example 2 was then tested for activity as an effective fungicide.

A uniform aqueous dispersion of the chemical made in Example 2 was first prepared. This dispersion was made by dissolving the chemical in a solution of acetone containing the surfactant TRITON X-155[1] (concentration 500 parts per million). Next, this solution was diluted with water (1:9) to obtain a stock solution of 10% by volume acetone and 90% by volume water with 50 ppm TRITON X-155 and the test chemical contained therein. This stock solution was diluted further with water/acetone mix to provide the desired concentration of the test material, if required.

[1] Manufactured by Rohm and Haas of Philadelphia, Pa. and is a polyether alcohol.

The aqueous solution containing the chemical was applied to various plants according to the methods stated below. These tests were designed to evaluate the ability of the chemical to protect non-infected foliage and eradicate recently established infection against major types of fungi such as anthracnose and potato late blight that attack above-ground parts of plants.

Cucumber Anthracnose

Two week old cucumber plants were sprayed while rotating the plants on a turntable with an aqueous solution that contained 260 parts per million by weight of the active chemical of Example 2. Simultaneously, the soil in each pot was drenched with the aqueous dispersion of the chemical in the amount of 25 lb/acre. After the spray deposit had dried, the plants were atomized with a suspension of cucumber anthracnose spores (*Collectotrichum lagenarium*) and placed in a moist chamber at 70° F. for 24 hours. After 5 days, the severity of pustule formation was rated on a scale of 0 (no inhibition) to 10 (complete inhibition). Subsequent tests were conducted as described except the material was tested for control at lower dosages. See Table I for the results of these tests.

TABLE I

FUNGICIDAL ACTIVITY AGAINST CUCUMBER ANTHRACNOSE

| Compound | 25 lb/acre drench & 260 ppm spray | 12.5 lb/acre drench | 6.3 lb/acre drench | 3.2 lb/acre drench | 130 ppm spray | 65 ppm spray | 33 ppm spray |
|---|---|---|---|---|---|---|---|
| Example 2 | 9 | 10 | 10 | 10 | 10 | 9 | 7 |

Potato Late Blight (*Phytophthora Infestans*)

Test plants were prepared by rooting cuttings from stock plants in perlite. When suitable root systems had initiated, the cuttings were transplanted into pots containing a sandy loam soil. The transplants were held until they had reached the 3–4 leaf stage and were then used for testing. An aqueous suspension of the test compound was applied to the soil as a drench in the amount of 25 lb/acre. After application of the test material, the plants were inoculated by spraying them with a suspension of sporangoia washed from agar cultures of *Phytophthora infestans*. The inoculated plants were held at 100% relative humidity and 20° C. for 24 hours, then held in a light room at 20° C. until disease control was assessed. Disease control was rated on a scale of 0 to 10 where 0=no control and 10=100% control. Subsequent tests were conducted as described except the material was tested for control at lower dosages. See Table II for the results of these tests.

TABLE II

FUNGICIDAL ACTIVITY AGAINST POTATO LATE BLIGHT

| Compound | 25 lb/acre drench | 12.5 lb/acre drench | 6.3 lb/acre drench |
|---|---|---|---|
| Example 2 | 10 | 10 | 6 |

Soil Fungicide Disinfectant Screen

Pythium ultimum was cultured on a sterile medium of corn meal and number 4 Zonolite in petri dishes. The culture was then blended with sterile soil. Ten pea seeds were pressed into the infested soil and covered with additional infested soil. Four controls were seeded: uninoculated, inoculated, chemical in uninoculated soil and standard chemical in inoculated soil. A mixture of the test material at 1040 ppm was added to each cup at a rate of 10 ml (25 lb/acre). The cups were held in closed plastic containers for 3 days before opening. Records were made of the emergence of seedlings and freedom of the hypocotyl from brown lesions after 10 additional days in the open. The chemical was rated depending upon the percentage of emergence and severity of lesions on survivors from 0 (severe infection on all plants) to 10 (no lesions). Subsequent tests were conducted as described except the material was tested for control at lower dosages. See Table III for the results of these tests.

TABLE III

| | FUNGICIDAL ACTIVITY AGAINST PYTHIUM | | | | | |
|---|---|---|---|---|---|---|
| Compound | 25 lb/acre | 12.5 lb/acre | 6.3 lb/acre | 3.2 lb/acre | 1.5 lb/acre | 0.75 lb/acre |
| Example 2 | 10 | 10 | 10 | 8 | 6 | 6 |

What is claimed is:
1. A compound having the formula:

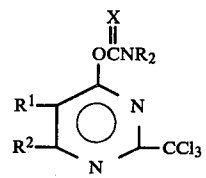

wherein X is an atom selected from the group consisting of oxygen and sulfur; R is a lower alkyl group having 1 to 4 carbon atoms or a phenyl group or $R_2$ is —($CH_2$)$_n$—, where n is 4 or 5; $R^1$ is hydrogen, a lower alkyl group having 1 to 4 carbon atoms, halo or nitro; and $R^2$ is a lower alkyl group having 1 to 4 carbon atoms or a haloalkyl group having 1 to 4 carbon atoms.

2. The compound of claim 1 wherein X is oxygen.
3. The compound of claim 2 wherein R is a lower alkyl group having 1 to 4 carbon atoms.
4. The compound of claim 3 wherein $R^1$ is hydrogen.
5. The compound of claim 4 wherein $R^2$ is a lower alkyl group having 1 to 4 carbon atoms.
6. The compound of claim 4 wherein $R^2$ is a haloalkyl group having 1 to 4 carbon atoms.
7. The compound of claim 3 wherein $R^1$ is halo.
8. The compound of claim 7 wherein $R^2$ is a lower alkyl group having 1 to 4 carbon atoms.
9. The compound of claim 7 wherein $R^2$ is a haloalkyl group having 1 to 4 carbon atoms.
10. The compound of claim 2 wherein R is a phenyl group.
11. The compound of claim 2 wherein $R_2$ is —($CH_2$)$_n$—, where n is 4 or 5.
12. The compound of claim 1 wherein X is sulfur.
13. The compound of claim 12 wherein R is a lower alkyl group having 1 to 4 carbon atoms.
14. The compound of claim 13 wherein $R^1$ is hydrogen.
15. The compound of claim 14 wherein $R^2$ is a lower alkyl group having 1 to 4 carbon atoms.
16. The compound of claim 14 wherein $R^2$ is a haloalkyl group having 1 to 4 carbon atoms.
17. The compound of claim 13 wherein $R^1$ is halo.
18. The compound of claim 17 wherein $R^2$ is a lower alkyl group having 1 to 4 carbon atoms.
19. The compound of claim 17 wherein $R^2$ is a haloalkyl group having 1 to 4 carbon atoms.
20. The compound of claim 12 wherein R is a phenyl group.
21. A method of controlling fungi which comprises contacting said fungi with a fungicidally effective amount of a compound having the formula:

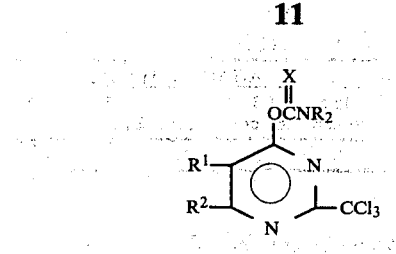

wherein X is an atom selected from the group consisting of oxygen and sulfur; R is a lower alkyl group having 1 to 4 carbon atoms or a phenyl group or $R_2$ is —$(CH_2)_n$—, where n is 4 or 5; $R^1$ is hydrogen, a lower alkyl group having 1 to 4 carbon atoms, halo or nitro; and $R^2$ is a lower alkyl group having 1 to 4 carbon atoms or a haloalkyl group having 1 to 4 carbon atoms.

22. The method of claim 21 wherein X is oxygen.

23. The method of claim 22 wherein R is a lower alkyl group having 1 to 4 carbon atoms.

24. The method of claim 23 wherein $R^1$ is hydrogen.

25. The method of claim 24 wherein $R^2$ is a lower alkyl group having 1 to 4 carbon atoms.

26. The method of claim 25 wherein said compound is 6-methyl-2-trichloromethyl-4-pyrimidinyl dimethylcarbamate.

* * * * *